(12) United States Patent
Jousma et al.

(10) Patent No.: US 8,578,539 B2
(45) Date of Patent: Nov. 12, 2013

(54) PRESSURIZED VALVE SYSTEM FOR DRIVING BRISTLE TUFTS

(75) Inventors: Hendrik Richard Jousma, Groningen (NL); Johannes Hotze Bernhard De Vries, Groningen (NL)

(73) Assignee: Koninklijke Philips N.V., Eindhoven (NL)

( * ) Notice: Subject to any disclaimer, the term of this patent is extended or adjusted under 35 U.S.C. 154(b) by 179 days.

(21) Appl. No.: 13/141,749

(22) PCT Filed: Dec. 9, 2009

(86) PCT No.: PCT/IB2009/055605
§ 371 (c)(1),
(2), (4) Date: Jun. 23, 2011

(87) PCT Pub. No.: WO2010/076702
PCT Pub. Date: Jul. 8, 2010

(65) Prior Publication Data
US 2011/0252584 A1    Oct. 20, 2011

Related U.S. Application Data

(60) Provisional application No. 61/141,363, filed on Dec. 30, 2008.

(51) Int. Cl.
*A46B 13/00* (2006.01)
(52) U.S. Cl.
USPC .............................. 15/22.1; 15/167.1; 15/201
(58) Field of Classification Search
USPC ................. 15/22.1, 22.2, 167.1, 201, 186
See application file for complete search history.

(56) References Cited

U.S. PATENT DOCUMENTS

| | | | |
|---|---|---|---|
| 4,346,492 A | 8/1982 | Solow | |
| 5,153,962 A | 10/1992 | Ritter | |
| 5,623,746 A | 4/1997 | Ichiro | |
| RE35,941 E * | 11/1998 | Stansbury, Jr. | 15/22.2 |
| 6,233,773 B1 | 5/2001 | Karge et al. | |
| 6,751,823 B2 | 6/2004 | Biro et al. | |
| 7,310,844 B1 | 12/2007 | Rehkemper | |
| 7,743,452 B1 * | 6/2010 | Tcholakov | 15/201 |
| 2002/0152565 A1 | 10/2002 | Klupt | |
| 2007/0145832 A1 | 6/2007 | Shimizu et al. | |

FOREIGN PATENT DOCUMENTS

| | | |
|---|---|---|
| DE | 202005003515 U1 | 7/2005 |
| EP | 1790312 A2 | 5/2007 |
| WO | 2006067749 A2 | 6/2006 |
| WO | 2006095222 A1 | 9/2006 |
| WO | 2007011112 A2 | 1/2007 |
| WO | 2007096167 A1 | 8/2007 |

\* cited by examiner

*Primary Examiner* — Shay Karls

(57) ABSTRACT

The dental cleaning appliance includes an appliance body (30, 73) which has a bristle field housing (32, 52) and fluid within the housing. A flexible membrane (34) is positioned within the housing, or in a fluid-tight relationship (54) within an opening (60) in the housing. A fluid pressure system involving either a dual piston system (22, 24, 28) or a pump and valve system (70, 68, 68) provides pressure on the fluid, wherein the pistons move alternately, or the valves open and close alternately, in such a manner to produce alternating pressure above and beneath the membrane, moving the membrane and the bristle field toward and away from the teeth.

15 Claims, 3 Drawing Sheets

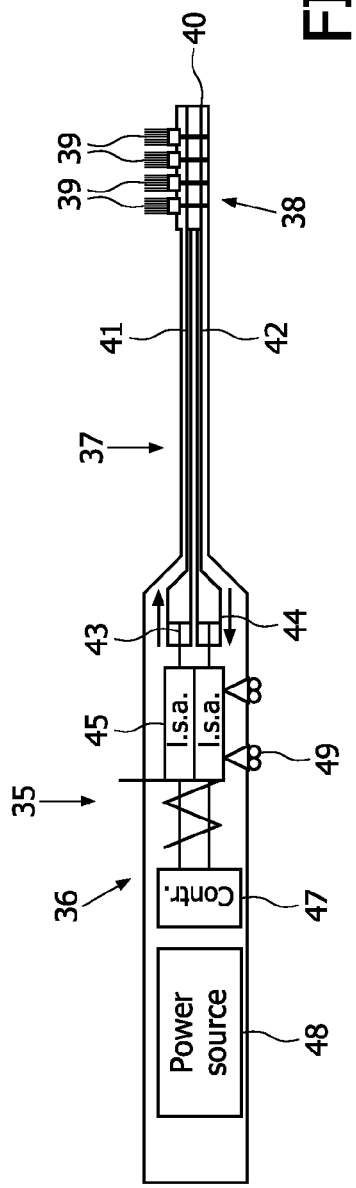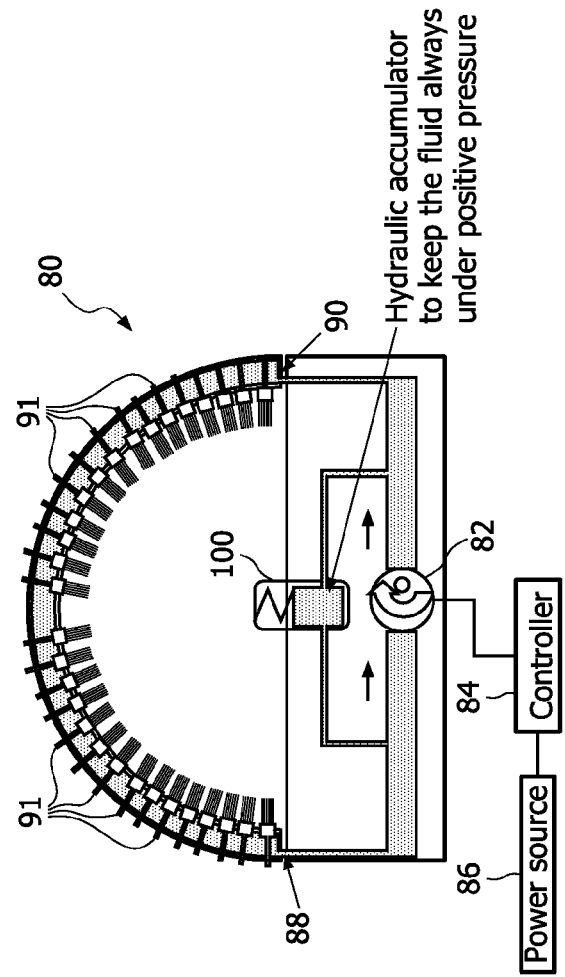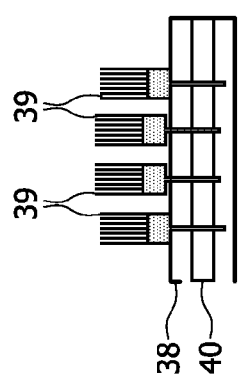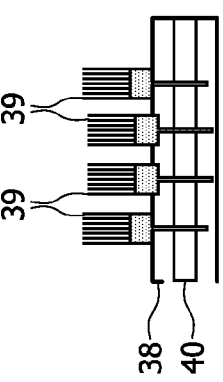

PRESSURIZED VALVE SYSTEM FOR DRIVING BRISTLE TUFTS

This invention relates generally to dental cleaning appliances, such as toothbrushes and mouthpieces, and more specifically concerns a system for driving the bristle tufts in those appliances toward and away from the teeth without producing cavitation sufficient to otherwise interfere with cleaning action.

In dental cleaning appliances, including both toothbrushes and mouthpieces, a particular bristle stroke useful for cleaning of dental surfaces is toward and away from the teeth in a tapping or light hammering type of action. Various ways of producing this particular motion are possible. However, one desirable way is by the use of fluid pressure. For effective cleaning action, a bristle stroke of between 0.9 and 3.22 mm and a frequency between 100 and 300 Hz has been found to be desirable. A known difficulty with such an arrangement, however, is that use of a pump to move fluid back and forth to produce the bristle stroke is both slow and energy consuming, as the inertial of the total fluid volume must be overcome. Furthermore, it is also known that with such a system the bristle tufts will move only very little, if at all, at the higher frequencies, i.e. above 100 Hz, due to cavitation effects in the fluid which are created by the pump action. A system for accomplishing fluid pressure-driven bristle tuft movement within the desired frequency range of 100-300 Hz is thus desirable.

One aspect of such a dental cleaning appliance, comprising: an appliance body, including a forward portion thereof having two separate interior channels and a bristle field housing at a distal end thereof; two moveable piston members positioned in a fluid-tight relationship within the two channels; a flexible membrane positioned within the bristle field housing, whereas the two channels extend above and below, respectively, the membrane, wherein fluid is present in the two channels, without fluid communication between them; a plurality of bristle tufts mounted on the membrane and extending sealingly through the housing; and an actuator assembly for moving the pistons alternately in a counter action within the two channels such that the membrane moves up and down, moving the bristle field toward and away from the teeth.

FIG. 3 is a cross-sectional view of the embodiment concept of FIG. 1 in a complete toothbrush.

FIGS. 4A and 4B are cross-sectional views showing the bristle tuft action of the toothbrush of FIG. 3.

FIG. 5 is a cross-sectional view of the embodiment concept of FIG. 1 in a mouthpiece.

Figure 1:
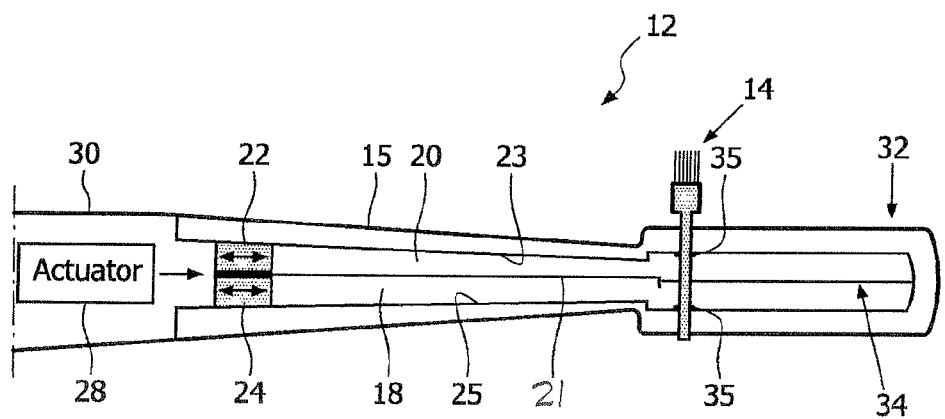
FIG. 1 is a simplified cross-sectional diagram showing one embodiment of a fluid pressure-driven appliance showing a single tuft.

FIG. 1 shows a first embodiment of a fluid pressure system for driving a bristle field toward and away from the teeth of a user, producing a tapping action against the teeth for cleaning thereof. The fluid pressure system can be used for moving either a toothbrush bristle field or a mouthpiece bristle field. FIG. 1 shows a brushhead portion 12 of a toothbrush and a bristle field 14 which for purposes of clarity includes only a single bristle tuft. Typically, a bristle tuft will include 90 or so individual bristles, while the bristle field for a toothbrush will typically include approximately 20 bristle tufts. While FIG. 1 shows a brushhead 12 which is more suitable in a toothbrush, similar arrangements can be made for a mouthpiece, as discussed in more detail below.

Brushhead portion 12 includes a neck section 15 which is divided into two channels 18 and 20 by a longitudinal member 21, positioned approximately midway between upper and lower neck section walls 23 and 25. Positioned in channels 18 and 20 in a fluid-tight relationship are pistons 22 and 24 which are moved back and forth by an actuation system shown generally at 28 positioned in a body portion 30 of the toothbrush.

Within a bristle field housing 32, which is located at the distal end of brushhead 12 and in fluid communication therewith, is mounted a flexible membrane 34. Membrane 34 in the embodiment shown is 10 mm wide by 20 mm long, which is approximately the size of a conventional toothbrush bristle field, and is approximately 0.1 mm thick in the embodiment shown. Membrane 34 is made of flexible rubber or other elastomeric material. The group of individual bristle tufts, illustrated by the single bristle tuft 14 shown, comprising a bristle field, are sealed to the membrane 34 and, to prevent fluid leakage, are sealed to the bristle field housing 32 at 35 as well. Positioned to the brushhead side of pistons 22 and 24 is fluid such as water, in both channels 18 and 20, while to the left of pistons 22 and 24 is air.

In operation, the pistons 22 and 24 move exactly counter-directionally to each other, i.e. 180° apart. As one piston moves to the right, the other piston moves to the left, and vice versa. When lower piston 24, for instance, moves to the right, an overpressure is created beneath membrane 34, due to the volume of channel 20 decreasing. At the same time piston 22 is moving to the left, resulting in under-pressure above membrane 34. This results in membrane 34 and the bristle tuft field moving upwardly in FIG. 1, in the direction of the teeth. Typically, the stroke will be approximately 3.2 mm, although the stroke could be somewhat different, i.e. within the range of 0.9-3.2 mm, and still produce effective cleaning.

Alternately, as upper piston 22 moves to the right toward the bristle field housing, creating an over-pressure on the upper surface of membrane 34, piston 24 will be moving to the left, resulting in an under-pressure on the lower surface of the membrane. This results in the membrane moving downwardly, with the bristle tuft field thus moving away from the teeth.

Continued repetitive action of the pistons 22 and 24 results in a rapid back-and-forth movement of the bristle tuft field, producing a tapping or light hammering-type action against the teeth, producing effective cleaning. The use of a double piston arrangement, with a consistent pressure (above ambient) within channels 18 and 20 and within the bristle tuft housing, prevents cavitation from occurring to any significant degree in fluid present in the mouth, thereby permitting higher bristle field frequencies, i.e. within the range of 100-300 Hz, with an effective stroke length.

FIG. 3 shows a more complete toothbrush 35. It includes a toothbrush body 36 and a brushhead 37 with a bristle tuft housing 38 at the distal end of the brushhead, a plurality of bristle tuft assemblies 39, positioned within housing 38 and mounted for up/down movement relative thereto. The bristle tuft holder portion of the bristle tuft assembly 39 is sealed relative to the bristle tuft housing 38. The bristle tuft holder further is connected to a flexible membrane 40 positioned in the housing 38.

Two channels 41, 42, filled with fluid, extend for the length of the brushhead 37, into bristle tuft housing 38. At the proximal ends of the fluid channels are pistons 43, 44, as in the above embodiment. They are counter-driven, typically with a 0.5 mm stroke, to press against the fluid in the channels, with the pressure always above ambient.

The pistons 43, 44 are moved separately by a linear actuator assembly 45, slidably moving along a track or a trolley 49 or the like. The system has a controller 47 with a power source 48. FIGS. 4A and 4B show the movement of the bristle tuft assemblies 39, up and down with membrane 40 as the pistons move counter to each other.

A mouthpiece embodiment is shown in FIG. 5. The mouthpiece shown at 80 includes a rotating DC motor 82 with an eccentric, controlled by a controller 84 with a power source 86. The motor 82 controls the movement of fluid alternately to an outer arch portion fluid connector 88 of the mouthpiece and an inner arch fluid connector 90. A plurality of bristle tuft assemblies 91 mounted on a flexible membrane, are located between the inner and outer arch portions so that as fluid pressure increases and decreases in alternating fashion on the membrane, movement of the bristle tuft assembly 91 toward and away from the teeth occurs, providing a tapping/light hammering action for cleaning of the teeth. A hydraulic accumulator 100 keeps the fluid under positive pressure, to avoid cavitation.

Figure 2:
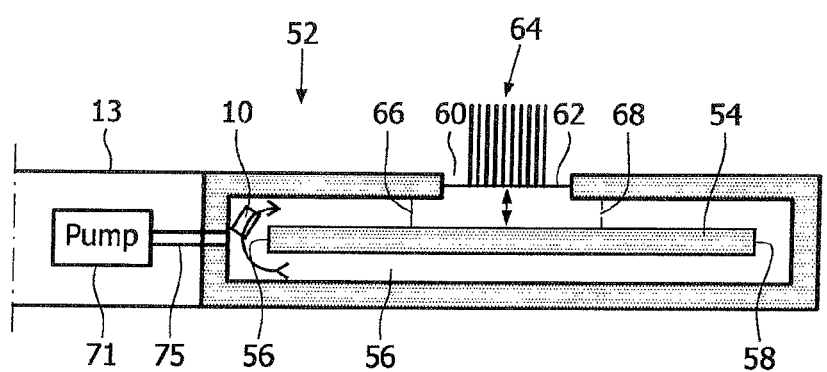
FIG. 2 is a simplified cross-sectional diagram showing another embodiment of a fluid pressure-driven tuft system.

FIG. 2 shows another embodiment for a fluid pressure-driven bristle field. FIG. 2 shows a cross-section of a brushhead portion of a toothbrush which includes a bristle tuft housing 52. Housing 52 in the embodiment shown is 20 mm long by 8-10 mm wide and 7 mm deep. It is made from plastic material, approximately 1 mm thick. Internally of housing 52 is a plate 54 which extends from side-to-side of the housing 52 but is positioned so that there is a space between ends 56 and 58 of the plate and the internal surface of housing 52. A fluid channel 56 is thus defined between housing 52 and plate 54.

Housing 52 includes an opening 60 which extends from side-to-side of the housing. In the embodiment shown, opening 60 is approximately 8 mm wide. Positioned in opening 60 is a flexible membrane 62. Membrane 62 is made from rubber or a similar flexible material, and in the embodiment shown is approximately 0.5 mm thick. A field of bristle tufts 64 is attached to the membrane. This can be done by various means, including thermal welding, gluing or molded into the membrane, or attached to a separate plastic sheet which in turn is attached to the membrane. In the embodiment shown, the bristle field is configured to be appropriate for a toothbrush embodiment.

Housing 52 includes two internal valves 66 and 68 which, in the embodiment shown, are rotational valves. Valves 66 and 68 are positioned between the inner surface of housing 52 and plate 54, adjacent the opposing edges of opening 60. Channel 56 is filled with fluid, with fluid access to membrane 60 being controlled by the position of valves 66 and 68. In one embodiment, a fluid pump 70 is located in the housing. Alternatively, a fluid pump 71 could be located in the body 73 of the appliance with a fluid line 75 to channel 56.

In operation, the fluid pump maintains a constant fluid pumping displacement in channel 56. The fluid could be liquid, such as water, or air. Valves 66 and 68 alternately open and close. When valve 66 is closed, fluid pressure will increase to the left of valve 66 and with valve 68 open, there will be an under-pressure (partial vacuum) created under membrane 62. The membrane will thus move inwardly of the housing, resulting in the bristle field 64 being pulled away from the teeth.

Alternately, when valve 66 is open and valve 68 is closed, an over-pressure is created beneath the membrane 62, forcing the membrane outwardly from the housing, resulting in the movement of bristle tuft field 64 toward the teeth.

An alternating action of valves 66 and 68 and hence membrane 62 results in a movement of the bristle tuft field 64 toward and away from the teeth, producing a tapping/light hammering action similar to that for the toothbrush embodiment of FIG. 1. With the constant fluid displacement in one direction produced by the fluid pump and the alternating action of valves 66 and 68, a bristle tuft field frequency of movement within the desired range of 100-300 Hz can be obtained, since there is little or no cavitation produced.

Figure 6:
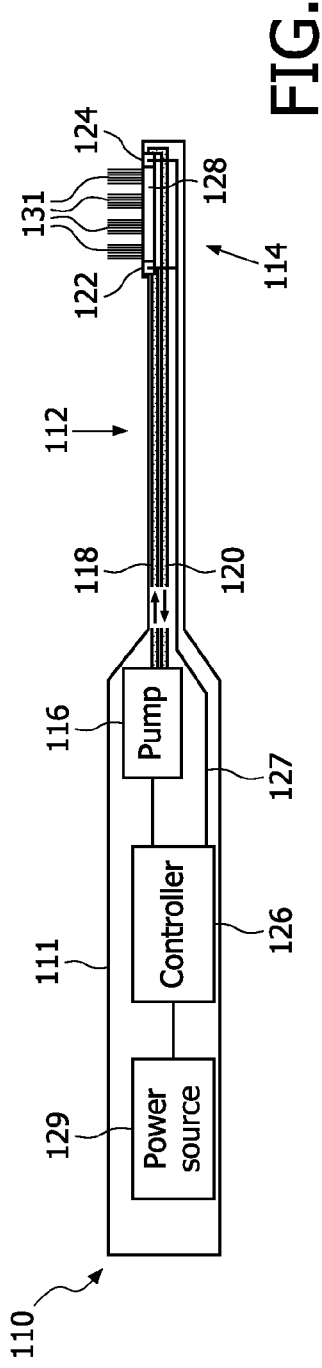
FIG. 6 is a cross-sectional view of the embodiment concept of FIG. 2 in a complete toothbrush.

FIG. 6 shows a complete toothbrush 110 for the embodiment of FIG. 2, including a toothbrush body 111, a brushhead portion 112 and a bristle tuft housing 114 at the distal end of the brushhead portion 112. A pump 116 moves fluid through two channels 118 and 120 to valves 122 and 124, which alternately open and close by action of controller 126, via a control line 127, which also controls pump 116. A plurality of bristle tuft assemblies 131 are mounted on a flexible membrane 128. A power source 129 powers controller 126.

Figure 7A:
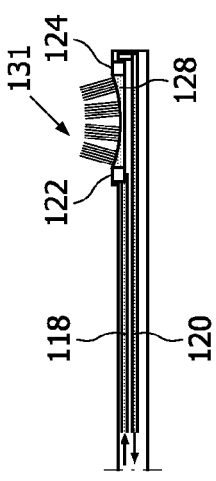
FIGS. 7A and 7B are cross-sectional views showing the bristle tuft action of the toothbrush of FIG. 6.
Figure 7B:
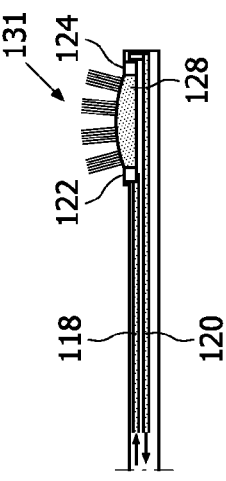

With valve 122 closed and valve 124 open, membrane 128 moves inwardly, with bristle tufts 131 moving away from the teeth, as shown in FIG. 7A. With valve 122 open and valve 124 closed, membrane 128 and the bristle tufts move outwardly, contacting (tapping) the teeth for cleaning action, as shown in FIG. 7B.

Figure 8:
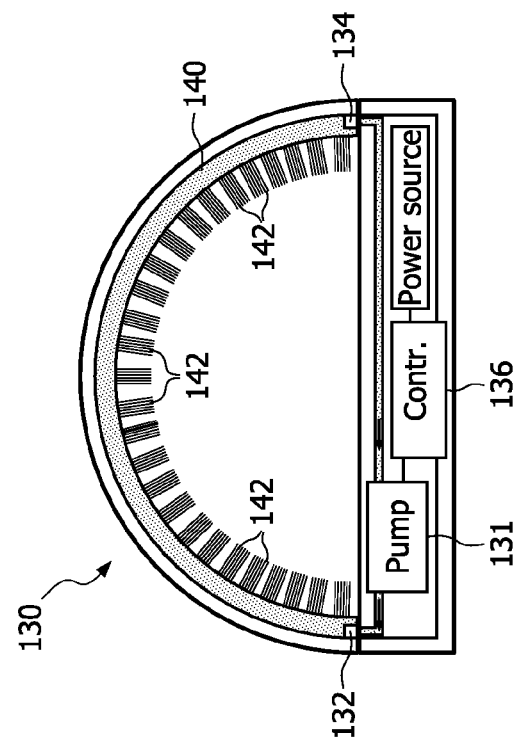
FIG. 8 is a cross-sectional view of the embodiment concept of FIG. 2 in a mouthpiece.

FIG. 8 shows a mouthpiece implementation 130 of the embodiment of FIG. 2. A pump 131 controls the movement of fluid in a dental arch to valves 132 and 134. The alternating action of the valves is controlled by a controller 136, as is the pump 131. The fluid action relative to a flexible membrane 140 on which a plurality of bristle tufts 142 are positioned will produce an in-and-out motion of the bristle tufts, toward and away from the teeth, producing a cleaning action.

Hence, several embodiments have been disclosed which provide a fluid pressure-driven action for moving a bristle tuft field at a desired frequency in the range of 100-300 Hz, wherein the embodiments are designed to substantially prevent cavitation, allowing the desired frequency to be achieved.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A dental cleaning appliance, comprising:
    an appliance body (30), including a forward portion thereof having two separate interior channels (18, 20) and a bristle field housing (32) at a distal end thereof;
    two moveable piston members (22, 24) positioned in a fluid-tight relationship within the two channels; wherein the two interior channels are defined by upper and lower walls, a common intermediate member and a common flexible membrane;
    the flexible membrane (34) being positioned within the bristle field housing, wherein the two channels extend above and below, respectively, the membrane, wherein fluid is present in the two channels, without fluid communication between them;
    a plurality of bristle tufts (14, 39) mounted on the membrane and extending sealingly through the housing; and
    an actuator assembly (28) for moving the pistons alternately in a counter action within the two channels such that the membrane moves up and down, moving the bristle field toward and away from the teeth.

2. The dental cleaning appliance of claim 1, wherein the frequency of movement of the bristle tuft field is within the range of 100-300 Hz.

3. The dental cleaning appliance of claim 1, wherein the stroke of the bristle tuft field moving toward and away from the teeth is within the range of 0.9-3.22 mm.

4. The dental cleaning appliance of claim of claim 1, wherein the dental cleaning appliance is a toothbrush.

5. The dental cleaning appliance of claim 1, wherein the dental cleaning appliance is a mouthpiece.

6. The dental cleaning appliance of claim of claim 1, wherein in operation one piston moves toward the bristle field housing while the other moves away from the bristle field housing, and vice versa.

7. A dental cleaning appliance, comprising:
- an appliance body (73), including a bristle field housing (52) filled with fluid, wherein the housing includes an opening (60) therein;
- a flexible membrane (62) positioned in the opening, the membrane having a fluid-tight relationship with the housing;
- a bristle tuft field (64) mounted on the membrane;
- a rigid member mounted within the housing, thereby defining a fluid passageway between an interior surface of the housing and the rigid member, passing underneath the membrane; and
- a pump and valve system (70, 66, 68) for maintaining pressure on the fluid in the housing, the valves positioned within the housing between the rigid member and the housing near opposing ends of the membrane and operating alternately such that fluid pressure alternately increases and decreases beneath the membrane, resulting in movement of the membrane and the bristle tuft field toward and away from the teeth.

8. The dental cleaning appliance of claim 7, wherein the frequency of movement of the bristle tuft field is within the range 100-300 Hz.

9. The dental cleaning appliance of claim 7, wherein the pump is located within the housing.

10. The dental cleaning appliance of claim 7, wherein the pump (71) is located within the appliance body, with a connecting line (75) between the pump and the housing.

11. The dental cleaning appliance of claim 7, wherein the fluid within the housing is liquid.

12. The dental cleaning appliance of claim 7, wherein the fluid within the housing is air.

13. The dental cleaning appliance of claim 7, wherein in operation, the valves open and close alternately, resulting in an alternating overpressure and underpressure beneath the membrane, producing the movement of the membrane and the bristle field toward and away from the teeth.

14. The dental cleaning appliance of claim 7, wherein the dental appliance is in the form of a toothbrush.

15. The dental cleaning appliance of claim 7, wherein the dental appliance is in the form of a mouthpiece.

* * * * *